US012690845B2

(12) United States Patent
Schröcker

(10) Patent No.: US 12,690,845 B2
(45) Date of Patent: Jul. 28, 2026

(54) ULTRASOUND SYSTEM IMAGING OF BLOOD FLOW

(71) Applicant: GE Precision Healthcare LLC, Waukesha, WI (US)

(72) Inventor: Gerald Schröcker, Salzburg (AT)

(73) Assignee: GE Precision Healthcare LLC

( * ) Notice: Subject to any disclaimer, the term of this patent is extended or adjusted under 35 U.S.C. 154(b) by 0 days.

(21) Appl. No.: 18/823,156

(22) Filed: Sep. 3, 2024

(65) Prior Publication Data

US 2026/0060655 A1     Mar. 5, 2026

(51) Int. Cl.
*A61B 8/06* (2006.01)
*A61B 8/00* (2006.01)

(52) U.S. Cl.
CPC .............. *A61B 8/5207* (2013.01); *A61B 8/06* (2013.01); *A61B 8/466* (2013.01); *A61B 8/488* (2013.01); *A61B 8/5246* (2013.01); *A61B 2576/023* (2013.01)

(58) Field of Classification Search
CPC ......... A61B 8/5207; A61B 8/06; A61B 8/466; A61B 8/488; A61B 8/5246; A61B 2576/023
See application file for complete search history.

(56) References Cited

U.S. PATENT DOCUMENTS

| | | | |
|---|---|---|---|
| 6,104,939 A | 8/2000 | Groner et al. | |
| 7,648,461 B2 | 1/2010 | Thiele | |
| 10,453,193 B2 * | 10/2019 | Schroecker | ............ A61B 8/488 |
| 11,701,081 B2 | 7/2023 | Wang et al. | |
| 11,944,497 B2 | 4/2024 | Du et al. | |
| 2006/0155187 A1 | 7/2006 | Zhao | |
| 2015/0038825 A1 * | 2/2015 | Abe | ..................... A61B 5/0095 |
| | | | 600/407 |
| 2015/0213597 A1 | 7/2015 | Oh | |
| 2015/0351675 A1 * | 12/2015 | Cheng | .................. A61B 5/0295 |
| | | | 600/323 |
| 2019/0117195 A1 | 4/2019 | Miles et al. | |
| 2019/0370947 A1 | 12/2019 | Tsujita | |
| 2019/0380685 A1 | 12/2019 | Schroecker | |

FOREIGN PATENT DOCUMENTS

| | | |
|---|---|---|
| CN | 117270584 | 12/2023 |
| JP | 2005300515 | 10/2005 |

OTHER PUBLICATIONS

EP application 25198663.4 filed Aug. 28, 2025—extended Search Report issued Jan. 15, 2026; 10 pages.

* cited by examiner

*Primary Examiner* — Amal Aly Farag
(74) *Attorney, Agent, or Firm* — MCANDREWS HELD & MALLOY, LTD; Daniel Bissing; David Bates

(57) ABSTRACT

An ultrasound system includes a transmitter, a receiver, a processor, and a display system. The transmitter emits ultrasonic energy towards a region of interest of a patient. The receiver receives ultrasonic signals reflected from the region of interest. The processor generates image data from the reflected ultrasonic signals, determines a height map according the reflected ultrasonic signals from the region of interest, and generates shaded image data by shading the image data according to the height map, such that regions of the image data that include blood flow are shaded to simulate a 3D effect, wherein the shaded effect includes transparent blood vessels through which the blood flow passes. The display system displays the shaded image data.

18 Claims, 13 Drawing Sheets

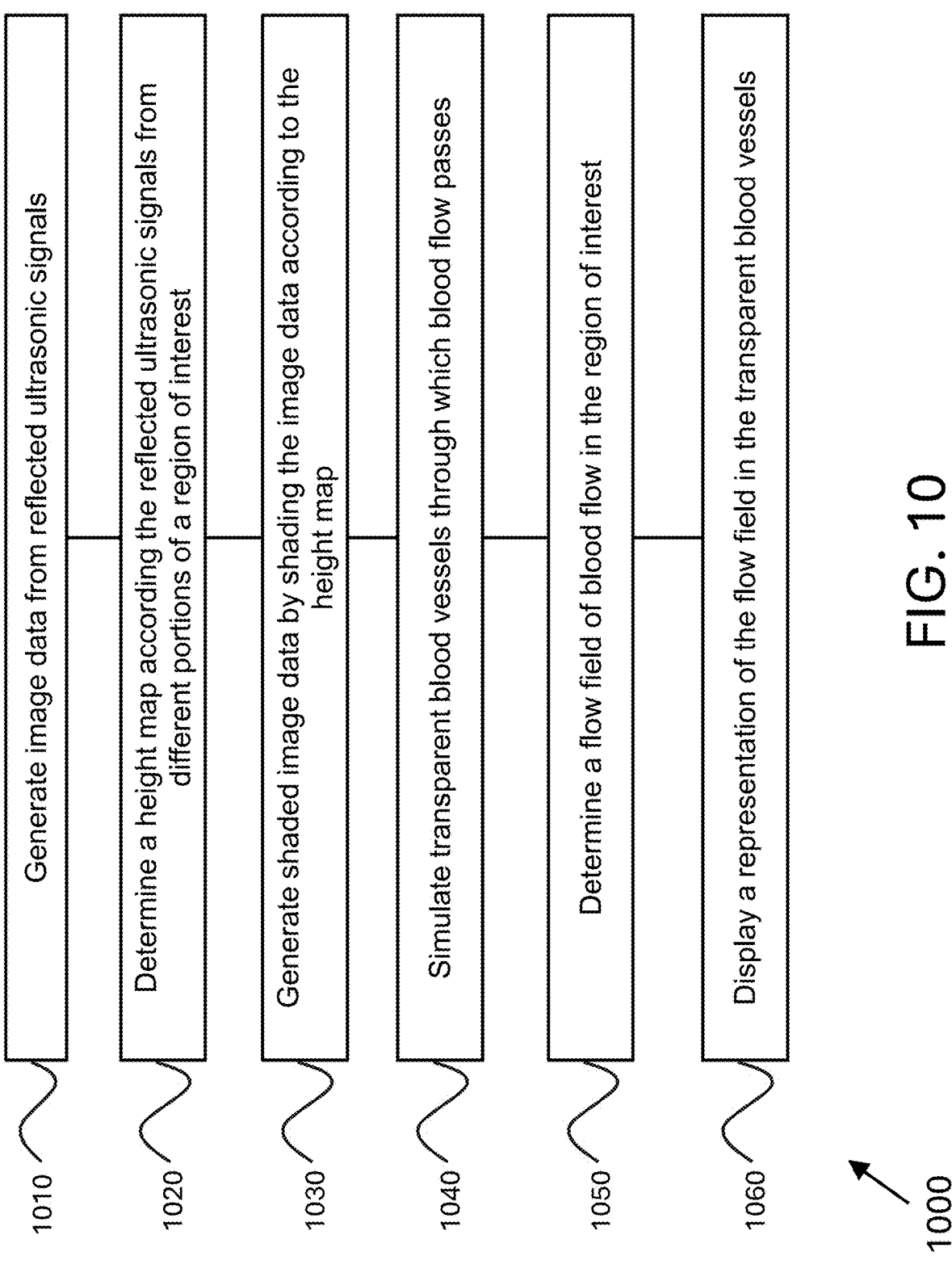

1010 Generate image data from reflected ultrasonic signals

1020 Determine a height map according the reflected ultrasonic signals from different portions of a region of interest 1030 Generate shaded image data by shading the image data according to the height map 1040 Simulate transparent blood vessels through which blood flow passes 1050 Determine a flow field of blood flow in the region of interest 1060 Display a representation of the flow field in the transparent blood vessels

ULTRASOUND SYSTEM IMAGING OF BLOOD FLOW

FIELD

Certain embodiments relate to ultrasound imaging. More specifically, certain embodiments relate to techniques for displaying blood flow.

BACKGROUND

Ultrasound image data (e.g., color Doppler image data) may include 2D scalar data (e.g., intensity values, power component values, or the like) which results in a flat 2D image that may be more difficult to interpret, thereby increasing a difficulty of diagnosing a patient using the flat 2D image. For example, more complex body structures may be difficult to recognize via a 2D image. As one example, 2D color Doppler images of different body structures may be difficult to use for diagnosis.

Additionally, with blood-speckle imaging (BSI) it is possible to acquire a 2D field of blood velocities in a patient's anatomy, such as in the chart.

Ultrasound Doppler imaging may be helpful to evaluate blood flow in the heart. Visualization of flow disturbances may be useful for understanding hemodynamics in, for example, children with congenital heart disease and for diagnosis and therapeutic planning in children with acquired and congenital heart disease. Such techniques may also be helpful to understand hemodynamics in a fetal heart.

BSI using conventional color Doppler technology may be limited due to Doppler angle dependency (display of only radial velocities) and aliasing (e.g., due to the Nyquist limit). BSI is a visualization technique intended to address these limitations in conventional color flow imaging. Exemplary aspects of BSI is described in U.S. Pat. No. 11,147,539, entitled "Methods and Systems for Blood Speckle Imaging," and filed on Sep. 18, 2017, the entirety of which is incorporated by reference, herein.

BSI is based on tracking of speckles generated by the moving blood cells from one frame to the next using a "best match" search algorithm. This allows for assessment of 2D blood velocity vectors without requiring injection of contrast agent and without the mathematical assumptions of approaches based on conventional color Doppler. Due to the relatively high rate of decorrelation of moving blood speckles, the acquisition frame rate must be relatively higher than that used in myocardial speckle tracking. Acquisition framerates for BSI may be in thousands of frames per second (FPS) range, but may be reduced, for example, to 60 FPS for display. To review the loops after acquisition, they may be displayed in slow motion.

To generate one frame for display on screen, at least three different sets of data can be processed. Exemplary sets of data include (1) B-mode image data (e.g., one channel of data (intensity), where intensity of reflected signals are represented by a level in a grayscale image), (2) color flow mapping data (color Doppler, or "CFM", with, for example, four channels including the power of reflected signals, turbulence, detected velocity in the X dimension, and detected velocity in the Y dimension), and (3) BSI data (for example, three channels, including velocity vectors in the X dimension, velocity vectors in the Y dimension, and a scalar quality assessment). All of this data can be acquired with the same frequency. The BSI data can be derived from the CFM data. To obtain this data, the ultrasound system can alternate between B-mode data acquisition phases and CFM data acquisition phases in a patient—e.g., a first B-mode data acquisition phase, a first CFM data acquisition phase, a second B-mode data acquisition phase, a second CFM data acquisition phase, etc.

For each of the B-mode and CFM data acquisition phases, receive beamforming can be performed similarly for B-mode data acquisition and CFM data acquisition) to focus on the receive lines. For one transmit/receive sequence in a phase to acquire CFM data, one line can be repeated multiple times (to form an ensemble) to reach higher pulse repetition frequencies (RPFs).

Subsequently, for data acquired in a given B-mode data acquisition phase, a processor can determine the intensities of the reflected signals. For data acquired in a given CFM data acquisition phase, high-pass filtering can be performed by the processor to filter only for reflections for regions in the ROI that are moving, and corresponding Doppler shifts can be determined.

For BSI processing, the processor can perform block matching between the ensemble subframes of the CFM frame and can compute from that the velocity vector (including both X- and Y-dimension components) and quality.

The three sets of processed data (for B-mode, CFM, and BSI) can then be saved to a cine buffer. For display on the display, the sets of processed data can be converted from beamspace (which is specific to the geometry of the probe) to a Cartesian space (e.g., a space corresponding to the display's pixel grid on screen) with scan conversion. The data can then converted from the different channels using a Red/Green/Blue (RGB) lookup table, and can be then shown on the display.

One challenge is how to visually present the blood velocity field, whether acquired by BSI or another technique, in a way that is intuitive for a clinician. Another challenge is to visually present the blood vessels to present a clear and intuitive display to the clinician.

SUMMARY

According to embodiments, an ultrasound system includes: a transmitter configured to emit ultrasonic energy towards a region of interest of a patient; a receiver configured to receive ultrasonic signals reflected from the region of interest; a processor configured to: generate image data from the reflected ultrasonic signals; determine a height map according the reflected ultrasonic signals from the region of interest, and generate shaded image data by shading the image data according to the height map, such that regions of the image data that include blood flow are shaded to simulate a 3D effect, wherein the shaded effect includes transparent blood vessels through which the blood flow passes; and a display system configured to display the shaded image data. The processor may be further configured to: determine a flow field of blood in the region of interest, wherein the flow field includes a plurality of vectors corresponding to a plurality of pathways of flows of the blood flow in the transparent blood vessels; and display a representation of the flow field in the transparent blood vessels. The representation of the flow field may include a plurality of arrows corresponding to the plurality of vectors. The representation of the flow field may include an animation including a plurality of frames, wherein advancement of the frames indicates movement of the blood along the pathways of flows in the flow field. The representation of the flow field may include virtual particles moving across the plurality of vectors. The processor may be further configured to display the flow field underneath an upper surface of the transparent blood vessels. The representation of the flow field may include different color information corresponding to different ones of the plurality of pathways along which the blood flows. The processor may be further configured to generate background ultrasound image data corresponding to tissue in the region of interest and displaying the shaded image data together with the ultrasound image data. The processor may be further configured to generate the transparent blood vessels according to the height map. The processor may be further configured to generate the transparent blood vessels according to a simulated light source and at least one of Snell's law and Beer's law. The processor may be further configured to generate the transparent blood vessels according to a Phong model.

According to embodiments, a method of ultrasound imaging includes: emitting, by a transmitter, ultrasonic energy towards a region of interest of a patient; receiving, by a receiver, ultrasonic signals reflected from the region of interest; generating, by a processor, image data from the reflected ultrasonic signals; determining, by the processor, a height map according the reflected ultrasonic signals from the region of interest, and generating, by the processor, shaded image data by shading the image data according to the height map, such that regions of the image data that include blood flow are shaded to simulate a 3D effect, wherein the shaded effect includes transparent blood vessels through which the blood flow passes; and displaying, by a display system, the shaded image data. The method may further include: determining, by the processor, a flow field of blood in the region of interest, wherein the flow field includes a plurality of vectors corresponding to a plurality of pathways of flows of the blood flow in the transparent blood vessels; and displaying, by the display system, a representation of the flow field in the transparent blood vessels. The representation of the flow field may include a plurality of arrows corresponding to the plurality of vectors. The representation of the flow field may include an animation including a plurality of frames, wherein advancement of the frames indicates movement of the blood along the pathways of flows in the flow field. The representation of the flow field may include virtual particles moving across the plurality of vectors. The method may further include displaying, by the display system, the flow field underneath an upper surface of the transparent blood vessels. The representation of the flow field may include different color information corresponding to different ones of the plurality of pathways along which the blood flows. The method may further include generating the transparent blood vessels according to the height map. The method may further include generating, by the processor, the transparent blood vessels according to a simulated light source and at least one of Snell's law and Beer's law.

These and other advantages, aspects and novel features of the present disclosure, as well as details of an illustrated embodiment thereof, will be more fully understood from the following description and drawings.

BRIEF DESCRIPTION OF SEVERAL VIEWS OF THE DRAWINGS

FIG. 10 is a flow chart illustrating exemplary steps that may be utilized for simulating transparent blood vessels, according to embodiments.

DETAILED DESCRIPTION

Figure 1:
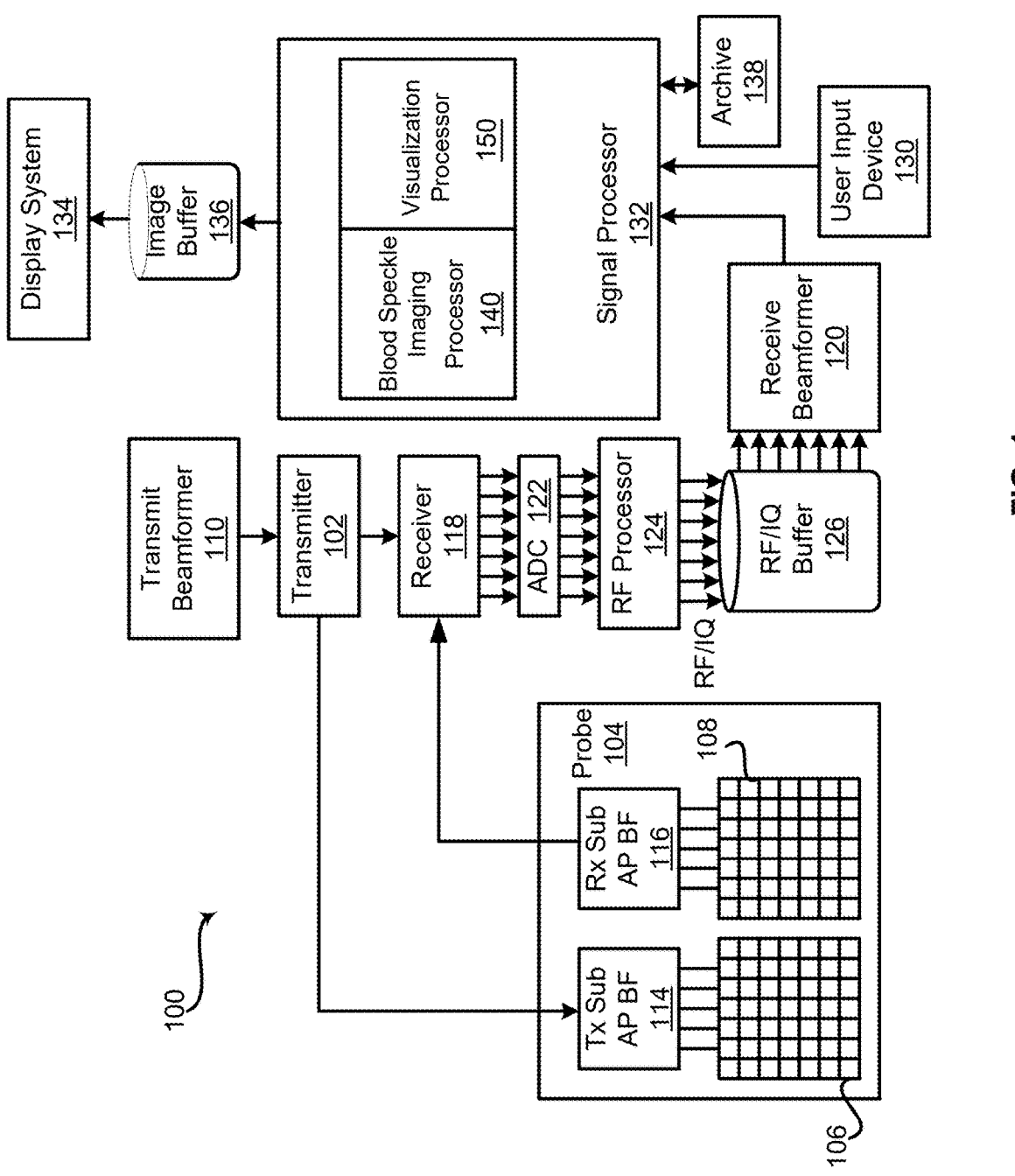
FIG. 1 is a block diagram of an exemplary ultrasound system that is operable to perform operations according to the techniques described herein, in accordance with various embodiments.

Certain embodiments herein relate to shading a 2D ultrasound image to simulate a 3D view, such as a 3D view of the blood vessels in the ROI, including embodiments that relate to simulating a transparent effect in the blood vessels in the ROI. Hereinafter, the transparent effect in the blood vessels may be referred to as transparent blood vessels or similar, unless specified otherwise. While blood vessels are described herein, techniques described herein may also be applicable to other anatomical structures.

The shading may be performed by using a gradient determined from height values correlated to image values of an ultrasound imaging dataset (which may be 1D, 2D, or 3D) used to generate the 2D ultrasound image. The transparent blood vessel simulation may be generated with light propagation calculations, thereby giving the blood vessels a liquid-like appearance. The transparent blood vessel simulation may be generated by simulating a light source external to the blood vessels (for example, as determined by the height values) and applying different principles, like Snell's law or Beer's law. Further, the reflection characteristics may be simulated by different techniques, such as application of illumination models like Phong, Cook Torrance, Blinn-Torrance-Sparrow, He-Torrance-Sillion-Greenberg, or the like.

With BSI, a 2D field of blood velocities (hereinafter, "flow field") may be obtained for a ROI. While BSI is described herein, other techniques for determining flow field may also be used in conjunction with the techniques described herein. According to embodiments, an animation is generated and displayed showing multiple paths of the blood particles in the flow field. The animation may correspond to the flow field determined for a given ultrasound image frame. The data used to determine the flow field may be drawn over a period of time across multiple frames—e.g., before, during, and/or after the frame for which the flow field will be determined. The animation may give the sense of motion for the clinician. The animation may represent blood flow direction and velocity. The animation may be displayed in the context of, or superimposed on ultrasound image data showing a patient's anatomy and ROI (e.g., B-mode image of a patient's heart). The image of the patient's anatomy may be a static image while being displayed with the animation. However, the image of the patient's anatomy may change in successive ultrasound image frames.

The animation may not be the result of a cine-style display of multiple frames in succession. The animation may be generated by using "virtual particles" along a given determined flow field path and advancing them along the direction of the path in successive animation frames. A given path can be determined according to a single flow-field vector, or the given path can be determined according to a combination of adjacent flow-field vectors (e.g., two, three, or more flow-field vectors arranged in series). The virtual particles may be placed at multiple random or pseudorandom locations along the path and may disappear (be removed) after a period of time (age) (e.g., once reaching the end of the path, at a predetermined distance from the end, at a predetermined distance from the start, and/or other distances). When a virtual particle disappears, it may be replaced by a new one at the previous particle's original start location, or at some other start location. Given virtual particles can have a speed that corresponds to a magnitude of a given corresponding flow field vector. Further given particles can have a direction that corresponds to a direction of a given corresponding flow field vector. The virtual particles may travel at a constant speed (advance along the path at a constant distance consistently across successive animation frames), or the speed may vary from particle-to-particle or path-to-path. Once the virtual particles have been repositioned, the display is updated with a new animation frame. The animation frames may be played in a loop to provide a continuous animated effect.

The paths themselves may be included in the animation. The virtual particles may be superimposed or displayed in context with the paths. The virtual particles and/or paths may be displayed in color. For example, the color scheme may be consistent with what is expected from color Doppler conventions. The virtual particles and/or paths may be overlaid on a color scheme, such as color Doppler conventions. It may be possible to display subsequent ultrasound image frame data and update the animation for the new frame accordingly.

According to embodiments, the animation or flow field representation may be presented within the transparent regions of the blood vessels, thereby simulating that the flow field is actually inside of the blood vessels, and thereby increasing the intuitive visualization of the blood flow through the blood vessels.

Aspects of the present disclosure have the technical effect of enhancing visualization of blood flow within an ROI of a patient's anatomy, such that a clinician may more readily and intuitively understand the nature of blood flows. Various embodiments have the technical effect of improving visualization and intuitive understanding of the patient's anatomy in the ROI by creating a 3D shaded effect where the blood vessels are simulated to have a degree of transparency. Further, various embodiments have the technical effect of combining the dynamic simulated movement of blood flow within the transparent blood vessels. The visualization may be for a given time slot (e.g., for one frame time duration), as opposed to over multiple time slots. In such a way, the clinician can readily and intuitively understand the behavior of blood flow at a given point in time, for example, the blood flow in a patient's heart at a given time during the cardiac cycle. Various embodiments have the technical effect of displaying helpful animations in context of the patient's anatomy displayed in a static ultrasound image, such that the clinician can understand where exactly particular blood flows are occurring. Various embodiments have the technical effect of providing animations in context of other information describing the blood flow, such as color information (e.g., color conventions used with known color Doppler imaging displays). Various embodiments have the technical effect of enhancing a clinician's understanding of blood flow in a patient's anatomy due to color alone.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be standalone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical, and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image (image data). However, many embodiments generate (or are configured to generate) at least one viewable image. In addition, as used herein, the phrase "image" is used to refer to an ultrasound mode, which can be one-dimensional (1D), two-dimensional (2D), three-dimensional (3D), or four-dimensional (4D), and comprising Brightness mode (B-mode or, also referred to as spatial B-mode), Motion mode (M-mode), Color Motion mode (CM-mode), Color Flow mode (CF-mode), Pulsed Wave (PW) Doppler, Continuous Wave (CW) Doppler, Contrast Enhanced Ultrasound (CEUS), and/or sub-modes of B-mode and/or CF-mode such as Harmonic Imaging, Shear Wave Elasticity Imaging (SWEI), Strain Elastography, Tissue Velocity Imaging (TVI), Power Doppler Imaging (PDI), B-flow, Micro Vascular Imaging (MVI), Ultrasound-Guided Attenuation Parameter (UGAP), Blood-speckle Imaging (BSI) and the like.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), Digital Signal Processor (DSP), Field-Programmable Gate Array (FPGA), Application-Specific Integrated Circuit (ASIC), or a combination thereof. A processor or processing unit may include multiple processors in the same location (e.g., integrated together in a single ASIC) or distributed over different locations. When there are multiple processors, they may communicate with other associated processors and/or work together to effect processing and computation.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to identify features in image data obtained from a patient (including a fetus), in accordance with various embodiments. The ultrasound system 100 comprises a transmitter 102, an ultrasound probe 104, a transmit beamformer 110, a receiver 118, a receive beamformer 120, analog-to-digital (A/D) converters 122, a radio frequency (RF) processor 124, a RF quadrature (RF/IQ) buffer 126, a user input device 130, a signal processor 132, an image buffer 136, a display system 134, and an archive 138.

The transmitter 102 may comprise suitable logic, circuitry, interfaces, and/or code that may be operable to drive an ultrasound probe 104. The ultrasound probe 104 may be a linear, convex, intracavitary, or phased array transducer. The ultrasound probe 104 may comprise a two dimensional (2D) array of piezoelectric elements or a piezoelectric layer. The ultrasound probe 104 may comprise a group of transmit transducer elements 106 and a group of receive transducer elements 108, that normally constitute the same elements. The group of transmit transducer elements 106 may emit ultrasonic signals through oil and a probe cap and into a target. In a representative embodiment, the ultrasound probe 104 may be operable to acquire ultrasound image data covering at least a substantial portion of an anatomy, such as a liver, kidney, pancreas, spleen, kidney, or any suitable anatomical structure. In an exemplary embodiment, the ultrasound probe 104 may be operated in a volume acquisition mode, where the transducer assembly of the ultrasound probe 104 acquires a plurality of parallel 2D ultrasound slices forming an ultrasound volume.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The ultrasound system 100 may further include a matching layer (not shown) having an acoustic impedance. Exemplary matching layer embodiments are disclosed in U.S. Pat. No. 7,757,389, filed on Jun. 25, 2007, the entirety of which is incorporated by reference herein. The matching layer may be positioned or located such that it is between the patient and the transducer elements 106, 108. The matching layer is configured to have an acoustic impedance between an impedance of a tissue of the anatomical region and an impedance of the material of the transducer elements 106, 108. The matching layer is configured to absorb waves reflected from the anatomical region due to the difference of the acoustic impedance between the anatomy at the region of interest and the impedance of the transducer elements 106, 108.

The ultrasound system 100 may further include a damping block (not shown) configured to absorb ultrasound energy. The damping block may be positioned behind the some or all of transducer elements 106, 108. Exemplary damping block embodiments are disclosed by "acoustic backing material 204" in U.S. Pat. No. 11,378,554, filed on Sep. 27, 2019, the entirety of which is incorporated by reference herein. The damping block may include various components with acoustic-dampening properties, such that at least a portion reflected ultrasonic waves received at the ultrasound system 100 are absorbed and not reflected back towards the patient by the ultrasound system 100. For example, the damping block may comprise a solidified blend of a backing polymer matrix, filler particles, and one or more additives (e.g., hardeners, crosslinkers), where the backing polymer matrix may be formed from a thermoplastic, thermosetting polymer precursors, or a resin, which may be selected in part for the acoustic-dampening properties thereof.

The plurality of A/D converters 122 may comprise suitable logic, circuitry, and interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces, and/or code that may be operable to demodulate the digital signals output by the plurality of A/D converters 122. In accordance with an embodiment, the RF processor 124 may comprise a complex demodulator (not shown) that is operable to demodulate the digital signals to form me/Q data pairs that are representative of the corresponding echo signals. The RF or I/Q signal data may then be communicated to an RF/IQ buffer 126. The RF/IQ buffer 126 may comprise suitable logic, circuitry, interfaces, and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select target structures for acquisition of images, input and/or select a region of interest, modify a region of interest, select regions of interest used to acquire images, a focused/zoomed volume, and the like. In an exemplary embodiment, the user input device 130 may be operable to configure, manage, and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera, and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (e.g., summed IQ signal) for generating ultrasound images for presentation on a display system 134. The signal processor 132 is operable to perform one or more processing operations according to a plurality of ultrasound modalities (such as B-mode, Doppler, and color Doppler modalities) on the acquired ultrasound scan data. In an exemplary embodiment, the signal processor 132 may be operable to perform display processing and/or control processing, among other things. Acquired ultrasound scan data, such as spatial B-mode data, may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a blood-speckle imaging (BSI) processor 140, and a visualization processor 150. The signal processor 132 may be capable of receiving input information from a user input device 130 and/or archive 138, generating an output displayable by a display system 134, and manipulating the output in response to input information from a user input device 130, among other things. The signal processor 132, the BSI processor 140, and/or the visualization processor 150 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 per second but may be lower or higher. As used herein, a "time" or "period of time" may correspond to one or more frames. The acquired ultrasound scan data may be displayed on the display system 134 at a display-rate that can be the same as the frame rate, or slower or faster. A sequence of images (for example of a patient's blood flow) may be displayed simultaneously. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a BSI processor 140 suitable for performing BSI calculations to determine a flow field of blood within a given portion of a patient's anatomy or a ROI therein. The BSI processor 140 may comprise suitable logic, circuitry, interfaces, and/or code that may be operable to use an ultrasound probe 104 to receive and process ultrasound image data corresponding to BSI and blood flow.

The signal processor 132 may include a visualization processor 150 for generating shading of the blood vessels in the ROI as will be further described. The visualization processor 150 may further generate transparencies of the blood vessels as will be further described. The visualization processor 150 may further generate depictions of the flow field, including animations or other symbols, such as arrows representing blood flow through the blood vessels, as will be further described. The visualization processor 150 may receive information from the BSI processor 140 relating to or regarding the flow field.

The display system 134 may be any device capable of communicating visual information to a user. For example, a display system 134 may include a liquid crystal display, a light emitting diode display, and/or any suitable display or displays. The display system 134 can be operable to present 2D ultrasound images, 2D sequential ultrasound images, biplane ultrasound images, biplane ultrasound slices extracted from 3D/4D volumes, rendered 3D/4D volumes, selectable target structures, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores 2D ultrasound images, 2D sequential ultrasound images, biplane ultrasound images, biplane ultrasound slices extracted from 3D/4D volumes, rendered 3D/4D volumes, instructions for acquiring ultrasound image data, instructions for producing sequential ultrasound images, instructions for generating sample sequential ultrasound images, instructions for classifying images as generated or real, instructions for providing feedback based on the classifying of images, instructions for determining that an objective function has been reached, instructions for generating an enhanced sequential ultrasound image, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

In accordance with embodiments herein, the system 100 may be configured to perform BSI to determine fluid flow in a patient, such as blood flow in a patient's anatomy (e.g., heart). Operation of the system 100 may be controlled by the BSI processor 140, either partially or for the entirety of system 100. The BSI processor 140 may be configured to instruct or cause the probe 104 to emit successive transmit beams from the transmit transducer elements 106. Echoes from the regions insonified by the transmit beams may be acquired by the receive transducer elements 108 of the ultrasound probe 104. The transmit beams are configured to acquire ultrasound data, including that from an ROI. The ROI may represent a portion of a patient anatomy, such as a heart, for example covering the chambers of the heart and the myocardia or the ROI may cover other parts of the venous system containing blood.

The BSI processor 140 may process the received ultrasound image data. The received ultrasound data may include, for example B-mode type of ultrasound data. The ultrasound data may be acquired during multiple time slots, such as frames. The ultrasound image data bay be clutter filtered temporally in order to enhance moving particles even if they are weak, such as blood. For example, the BSI processor 140 may generate sub-images based on the received ultrasound data. The sub-images may represent the ultrasound data that includes a speckle pattern. The BSI processor 140 may apply a clutter filter to the speckle pattern. Clutter filtering may occur during the beamforming and/or subsequent to the beamforming. Clutter filtering may extract a blood component from the sub-image and calculate a time delay between transmit and receive beamforming. The BSI processor 140 may apply the time delay correction to the speckle pattern within the sub-image to enhance motion of the speckle tracking. Clutter filtering may be performed on a sub-image prior to identifying the speckle tracking. The speckle pattern may be used to track the motion of the blood within the chambers of the heart or other parts of an ROI, but it may also be used to track moving tissue, for instance myocardial motion of the heart. The motion of the speckles over time may be tracked by the BSI processor to form a flow field, for example, including velocity data. For example, the motion of the speckles can represent a flow field indicative of a 2D dimensional blood velocity field. Further details and embodiments of BSI are described in U.S. Pat. No. 11,147,539, which is incorporated by reference in its entirety, herein.

Figure 2:
FIG. 2 is an exemplary ultrasound image data and a region of interest (or ROI) therein.

FIG. 2 is exemplary B-mode image data 200 and a region of interest 210 therein. The B-mode image data 200 shows a static image including a portion of a patient's heart. The B-mode image data 200 may be presented on a display system 134 for viewing by a user. The B-mode image data 200 may be displayed in context with other image data (e.g., color Doppler image data), for example, as a background. As techniques herein enhance visualization of blood flow through vessels, the B-mode image data 200 can provide context of the position of the blood vessels and blood flow by displaying images of surrounding and proximate tissue (e.g., muscles of the heart). The region of interest 210 defines a subset 220 of the B-mode image data 200. The region of interest 210 may be drawn and/or positioned by a user in the B-mode image data 200 according to clinical purposes. The region of interest 210 may be drawn and/or positioned by the user through user input device 130. As generally disclosed herein, B-mode image data 200 is used as an example, although other types of image data could be used in accordance with techniques described herein. Such other types of image data include Doppler image data or color Doppler image data. In systems that are multimodal (e.g., are capable of obtaining B-mode image data and Doppler image data), multiple types of image data may be used in combination.

Figure 3:
FIG. 3 depicts blood flow generated with color Doppler image data, and is presented in context with the ultrasound image data of FIG. 2.

FIG. 3 depicts B-mode image data 200, where the subset 220 of the B-mode image data 200 is displayed in context with color Doppler image data 230. The color Doppler image data 230 may show blood flow through vessels in the patient in the region of interest 210. The color Doppler image data 230 may be colorized to indicate whether the blood flow is towards or away from the ultrasound probe 104. As shown, the direction and degree of blood flow towards the probe 104 is colorized with red and yellow, and shades thereof according to the speed of the blood flow towards the probe 104, as indicated in the legend in the upper left of FIG. 3. As shown, the direction and degree of blood flow away the probe 104 is colorized with blue, and shades thereof according to the speed of the blood flow away from the probe 104, as indicated in the legend in the upper left of FIG. 3. Different color schemes may be used to indicate the direction and speed of the blood flow with respect to the probe 104. Further, the color Doppler image data 230 may not be used, and a different type of image data may be displayed (for example, in the regions where the color Doppler image data 230 would otherwise be). Such other types of image data may be generated by the ultrasound system 100 using modalities such as B-mode imaging, or others such as the modalities described herein.

Figure 4:
FIG. 4 depicts shading of the blood flow shown in FIG. 3, and is presented in context with the ultrasound image data of FIG. 2.

FIG. 4 is similar to FIG. 3, except the color Doppler image data 230 has been shaded to form shaded color Doppler image data 240. Again, other types of image data may be used, such as those generated by other ultrasound modalities. The shaded color Doppler image data 240 may provide a 3D effect from underlying 2D data. Some techniques for shading are disclosed in U.S. Pat. No. 10,453,193, the entirety of which are incorporated by reference, herein. Shaded color Doppler image data 240 may be generated by determining a height map of the Shaded color Doppler image data 240.

Figure 8:
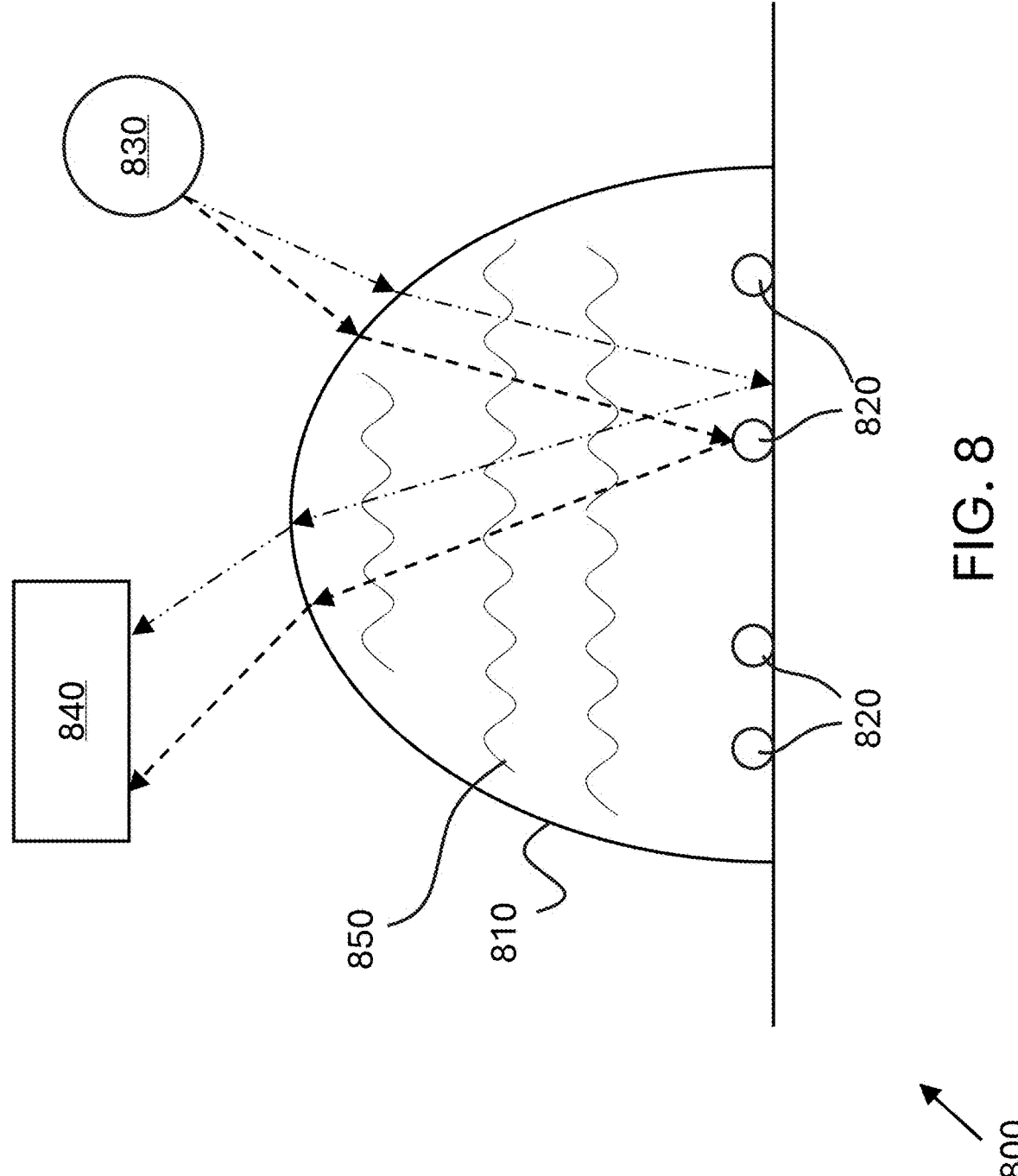
FIG. 8 depicts a virtual system for simulating transparent blood vessels, according to embodiments.

To determine the height map (an example of which is shown in FIG. 8, which will be further described), image values of pixels in the color Doppler image data 230 may be converted to a corresponding height value using a relationship (e.g., model). In one example, the relationship for converting each image value (e.g., the power or raw intensity value) to a height value may be a linear relationship. In another example, the relationship or model for converting each image value to a height value may be a monotonic function, such as a logarithmic or sigmoid function that is a function of the image value and then outputs a height value. In some embodiments, the height values may be used to create a height map or relief image that represents a height field of the color Doppler image data 230. In this way, the image values may be represented as height values.

A gradient may then be calculated for each height value. An example equation for computing the gradient, including a surface normal, is shown by Equation 1:

$$| \vec{n}(x, y) = |\nabla h(x, y)| = \left\| \begin{pmatrix} \dfrac{\partial h}{\partial x} \\ \dfrac{\partial h}{\partial y} \\ r \end{pmatrix} \right\| = \left\| \begin{pmatrix} h(x-1, y) - h(x+1, y) \\ h(x, y-1) - h(x, y+1) \\ r \end{pmatrix} \right\| \qquad \text{Equation 1}$$

where x, y is a position in the image data, where n(x,y) are the surface normal vectors at the pixels, $\nabla$ is the gradient, h(x,y) is the scalar height value function (which represents a scalar valued function, such as B-mode intensity, Doppler power, or the like) at position (x,y), and r is a constant defining the roughness of the resulting gradient field.

The normal of the height value h(x,y) at the position (x,y) is computed by computing the norm of the gradient at this position. The gradient is defined by the partial derivatives in the direction of x and y. The x component is computed with central differences in the x direction. The y component is computed with central differences in the y direction. The z component is the constant r. In this way, determining a gradient for each height value h(x,y) is based on a difference in height values of adjacent pixels in the 2D image data (e.g., h(x−1,y), h(x+1,y), h(x,y−1), and h(x,y+1)).

In computing the norm (length=1) of the gradient, the influences of the roughness constant varies for different gradient lengths. For example, if the position (x,y) is in a homogenous region (e.g., a region of the image with little or no variation between height values of adjacent pixels), the x,y components of the gradient are smaller and r is the dominating factor, thereby resulting in a normal vector pointing approximately in the z direction n=(0,0,1). In another example, if the position (x,y) is in a greatly varying area (e.g., a region of the image with larger variation between height values of adjacent pixels), the x and/or the y component of the gradient is bigger and r has less influence, thereby resulting in the normal pointing slightly upwards in the direction of the change. As one example, by representing the image values as height values, computing the gradient of the 2D image includes computing the surface normal of the height field consisting of the height values.

After computing the gradient of each height value, h(x,y), shading (e.g., surface shading) is applied to the 2D image data using the surface normal vector, n(x,y), at each position (x,y) of the image data. After the application of surface shading using the gradient, the resulting image data is the shaded color Doppler image data 240, such as that shown in FIG. 4, which includes shading at each location. The shading model used to generate the shaded color Doppler image data 240 may be one or more shading models, such as a diffuse specular shading model, a Phong reflection model, a Blinn-Phong shading model, a specular highlight shading model, or the like. As one example, the Phong reflection model (also referred to as Phong illumination, Phong lighting, or Phong shading) is a model of the local illumination of points on a surface (e.g., pixels on the 2D image). The Phong reflection model describes the way a surface reflects light as a combination of the diffuse reflection of rough surfaces with the specular reflection of shiny surfaces. The model also includes an ambient term to account for the small amount of light that is scattered about the entire scene.

Figure 5:
FIG. 5 depicts transparent blood vessels corresponding to the shaded blood flow in FIG. 4, and are presented in context with the ultrasound image data of FIG. 2, according to embodiments.

FIG. 5 illustrates the image data 200 with transparent blood vessels 250. The transparent blood vessels 250 are simulated from the color Doppler image data 230 or the shaded color Doppler image data 240. Again, image data generated by other ultrasound modalities may be used, aside from color Doppler image data. The degree of transparency of the transparent blood vessels 250 may be varied, for example, by a user through the user input device 130.

One technique for generating the transparent blood vessels 250 is shown in FIG. 8, which shows an example of a cross-section of a blood vessel, for illustrative purposes. FIG. 8 shows a virtual system, including a portion of a height map 810, representations of a flow field 820 of blood flowing through the blood vessel (as will be discussed in more detail below), a simulated light source 830, a simulated camera 840, and simulated fluid 850 in the blood vessel. The height map 810 virtually defines the extent of an upper portion of a cross-section of a blood vessel. The lower contour shown is a straight line, and is a reference plane from which the height map 810 is generated. The height map may be determined according to the techniques described above. For simulation purposes, and for the example of FIG. 8, the lower contour may be a straight line, although it is understood that a cross-sectional contour of a blood vessel is not typically a straight line. Other shapes for lower contours may be used.

The simulated light source 830 may be a point source, directional (e.g., parallel rays like the sun), spot (cone of rays), or the like. Aspects of the simulated light source 830 include position of the light source, direction of light rays, color of the light, intensity, cone opening angle, and/or the like. A user may be able to adjust one or more aspects of the simulated light source 830, for example, through the user input device 130. The simulated light source 830 emits virtual rays towards the blood vessel. The virtual rays are simulated to refract at the interface of the blood vessel (e.g., the location of the height map). The virtual rays may be simulated to refract according to Snell's law. To simulate the refraction, the index of refraction of the simulated fluid 850 in the blood vessel is a value, for example, between 1-2 such as for example 1.33. The index of refraction of the virtual medium outside of the blood vessel is a value such as for example 1. These indices may be adjustable by the user, for example, through the user input device 130.

The virtual rays are simulated to reflect, either off of the lower contour or off of the representations 820 of the flow field. After the virtual rays are simulated to reflect off of the lower contour or off of the representations 820, they are again simulated to refract as they exit the blood vessel (e.g., the top of the height map 810) and travel towards the camera 840.

As shown in FIG. 8, the representations 820 may be at or immediately above the lower contour of the blood vessel. However, the representations 820 may be at one or more different altitudes, either underneath the height map 810, or at or above the height map 810. The representations 820 themselves may be shaded to simulate a 3D appearance. The representations 820 may be opaque and/or have a degree of transparency. If transparent, the degree of transparency of the representations 820 may correspond to an aspect of the flow field, such as the aspects described herein—e.g., volume or velocity.

The simulated camera 840 may use parallel projection or perspective projection. Parallel projection may be used to avoid any foreshorting effect. The position of the simulated camera 840 may be adjustable.

The color of the rays when they arrive at the simulated camera 840 may be adjusted according to the nature of the simulated fluid 850 and/or the distance that the rays travel through the blood vessel. One such technique for adjustment of the color of the rays may involve calculations according to Beer's law, where absorbance is a function of molar absorptivity, the length of the path through the medium, and the concentration of chemical species that absorb light.

In general, the simulated transparencies may be generated according to various principles, including refraction as described by Snell's law, absorption for example as described by Beer's law, the amount of reflected vs. refracted light for example as described by Fresnel's law, caustics, subsurface scattering, or similar, or a combination of two or more of the foregoing principles.

The degree of transparency may be adjustable, for example, by a user through user input device 130. At the extreme end of adjustable transparency, the blood vessel may be completely opaque (i.e., no transparent simulation) or completely transparent (i.e., the upper surface of the blood vessel is not viewable).

The depiction of the transparencies may vary over time, and may be displayed in a cine-style animation that advances through a sequence of ultrasound image data frames. For example, the shape or height map corresponding to blood vessels may vary over time, and cine-style animation may indicate to the clinician how those vessels change shape. Blood flow varies over time as the heart pumps blood. Also as the position and angle of the probe relative to the body changes the perceived shape and position of the vessels change. Such factors may lead to the height map of blood vessels to vary.

As shown in FIG. 5, the transparent blood vessels 250 may be displayed in context with background ultrasound image data, such as that shown in FIG. 2. The subject matter simulated below the transparent blood vessels 250 may be background image data, a constant pixel colors across the area, or an arbitrary pattern or depiction. Again, while color Doppler image data is shown as an example, other types of ultrasound image data, such as B-mode image data may be used for simulating transparent blood vessels.

Figure 6:
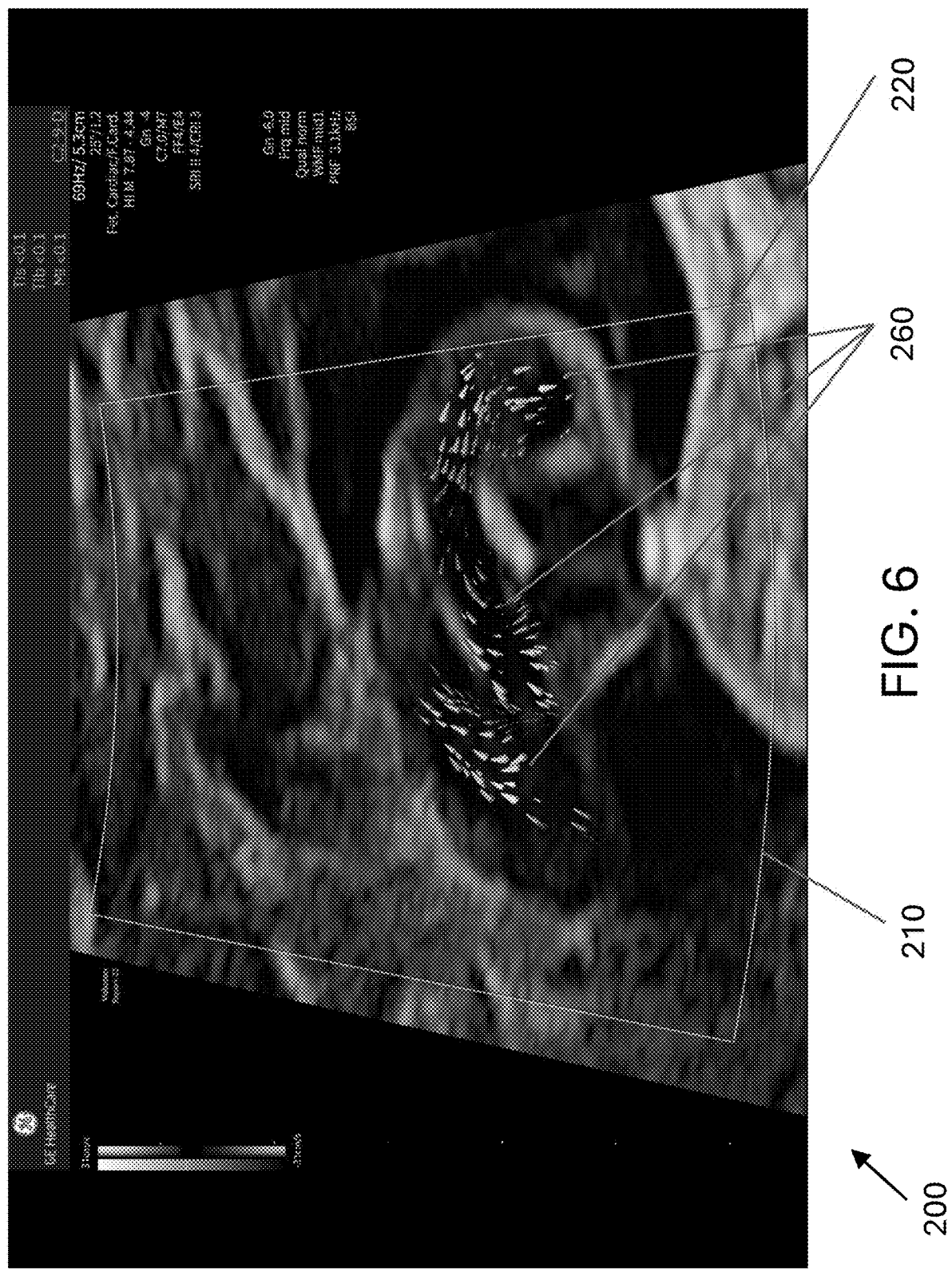
FIG. 6 depicts representations of the flow field of blood through blood vessels and corresponds to the blood flow depiction in FIG. 3, and are presented in context with the ultrasound image data of FIG. 2.

FIG. 6 illustrates representations 260 of the flow field in combination with a background image, according to embodiments. The representations may be similar to representations 820, disclosed in context of FIG. 8. As depicted, the background image includes B-mode image data, although image data from other ultrasound modalities (as described herein) may be used for the background image. FIG. 6 does not show blood vessels with simulated transparency. The representations 260 may be static or may be animated, such as the animations described in U.S. Ser. No. 18/736,060, filed on Jun. 6, 2024, the entirety of which is incorporated by reference herein. Examples of static representations 260 include arrows showing the direction or magnitude of blood flow in a particular region proximate the representations. The width and/or length of the arrows may indicate other characteristics of blood flow, including magnitude, velocity, or acceleration. The static representations 260 may be animated in a cine-style animation that advances across multiple ultrasound image data frames, thereby showing the dynamic nature of blood flow through the vessels over time.

An actual animation represented by the animation representations 260 are not visible in FIG. 6, which is a static image. The shapes of the animation representations 260 each correspond to a sub-flow animation. A given sub-flow animation 260 in the animation representation animates the flow of blood according to one or more flow-field vectors (e.g., only one flow-field vector or two or more flow-field vectors in series). Via animation, a given sub-flow animation 260 indicates one or more characteristics of the blood flow in a limited area of the region of interest 210. One such characteristic is a pathway corresponding to a direction along which blood flows. Another such characteristic is a volume of blood flow flowing along the pathway. Another such characteristic is the speed of the blood flow flowing along the pathway. Another such characteristic is the rate of acceleration or deceleration of blood flow along the pathway. Another such characteristic is the vorticity of the blood flow. Another such characteristic is the energy loss of the blood flow. Such characteristic(s) may be determined using blood speckle imaging data. Exemplary aspects of blood speckle imaging are described in U.S. Pat. No. 11,147,539, entitled "Methods and Systems for Blood Speckle Imaging," and filed on Sep. 18, 2017, the entirety of which is incorporated by reference, herein.

A flow field may be generated from the blood speckle imaging data or by other imaging techniques. The flow field may be two dimensional or three dimensional (i.e., the vector may correspond to a two-dimensional region of interest or a three-dimensional region of interest). The flow field may encode, for each of a plurality of vectors therein, one or more characteristics (e.g., direction, speed, volume, speed, and/or acceleration/deceleration) of the blood flow in specific regions of the anatomy. The flow field may represent blood flow during one slot (e.g., one frame). Such a slot may have a duration of between approximately 8-20 ms. While the flow field may represent blood flow during one slot, the flow field may be generated from data obtained in earlier slot(s) (e.g., frame(s)) or subsequent slot(s) (e.g., frame(s)), in addition to the slot for which the flow field will be determined.

The animation representations 260 correspond to a single slot, which in the example, is a single frame. The animation is formed from multiple animation frames, which are different than ultrasound imaging frames. The animation may not be the result of a cine-style display of multiple ultrasound imaging frames or slots in succession. The animation may be generated by using "virtual particles" along a given determined flow field path and advancing them along the direction of the path in successive animation frames. The virtual particles may be placed at multiple random or pseudorandom locations along the path and may disappear (be removed) after a period of time (age) (e.g., once reaching the end of the path, at a predetermined distance from the end, at a predetermined distance from the start, and/or other distances). When a virtual particle disappears, it may be replaced by a new one at the previous particle's original start location, or at some other starting location. The virtual particles may travel at a constant speed (advance along the path at a constant distance consistently across successive animation frames), or the speed may vary from particle-to-particle or path-to-path. Once the virtual particles have been repositioned, the display is updated with a new animation frame. The animation frames may be played in a loop to provide a continuous animated effect. A user may be able to interact with the ultrasound system 100 (e.g., through user input device 130) to pause or start the animation. The rate of animation frame advancement may be adjustable, e.g., by a user through the user interface device 130.

The paths themselves may or may not be included in the animation. The paths may be straight or may have other shapes, such as a curved shape. A given path may correspond to a single directional vector from the flow field, or may correspond to a plurality of adjacent vectors from the flow field.

The virtual particles may be superimposed or displayed in context with the paths, or displayed without the paths. The virtual particles and/or paths may be displayed in color, as shown. For example, the color scheme may be consistent with what is expected from color Doppler conventions (e.g., blue for movement away from the transducer, where lighter shades of blue correspond to faster flows away from the transducer, and red for movement towards the transducer, where lighter shades of red correspond to faster flows towards the transducer). The virtual particles and/or paths may be overlaid on a color scheme, such as color Doppler conventions, but otherwise have a different color scheme (e.g., grayscale scheme or black/white scheme). It may be possible to display subsequent ultrasound image frame data and update the animation for the new frame accordingly. A succession of animations corresponding to a succession of frames may be displayed over time. In this scenario, at least a portion of the animation (e.g., one loop of animation frames) may be displayed before automatically moving to the next frame. As such, the speed of display of the frames may be slowed down from the acquisition rate. The duration of display of each frame may be long enough to allow the clinician to appreciate the nature of the animated blood flow (e.g., presenting each frame for a period of time of at least two seconds). The rate of frame advancement may be adjustable, e.g., by a user through the user interface device 130.

In addition to the animated direction of flow along a path, other characteristics of the flow field may be animated using different animation aspects. Such aspects include sizes of virtual particles, shapes of virtual particles, changing shapes of virtual particles, numbers of visual particles simultaneously travelling along a path, spacing (density) of virtual particles, colors of virtual particles (either static colors or changing colors of given virtual particles), speeds of virtual particles, and/or acceleration/deceleration of speeds (e.g., as assessed in view of previous slots) of given virtual particles. For example, a velocity characteristic may be represented by one or more of a size of a virtual particle (e.g., a faster flow may be indicated by a larger virtual particle, either in length and/or in width), a shape of a virtual particle (e.g., a faster flow may be indicated by a particle having a longer taper on its tail), the number or density of virtual particles traveling along a given path or within a given sub-region (e.g., a faster flow may correspond to more or denser virtual particles), the color of a virtual particle (e.g., faster flows may correspond to deeper colors), and/or the speed of a virtual particle (e.g., faster flows may correspond to faster virtual particles). As another example, a volume characteristic may be represented by one or more of a size of a virtual particle (e.g., a larger flow may be indicated by a larger virtual particle), a shape of a virtual particle (e.g., a larger flow may be indicated by a particle having a longer length), the number or density of virtual particles traveling along a given path or within a given sub-region (e.g., a larger flow may correspond to more or denser virtual particles), the color of a virtual particle (e.g., larger flows may correspond to deeper colors), and/or the speed of a virtual particle (e.g., larger flows may correspond to faster virtual particles). As another example, the acceleration/deceleration of a virtual particle may be indicated by a change in speed of the virtual particle, in addition to the other techniques described above.

Figure 7:
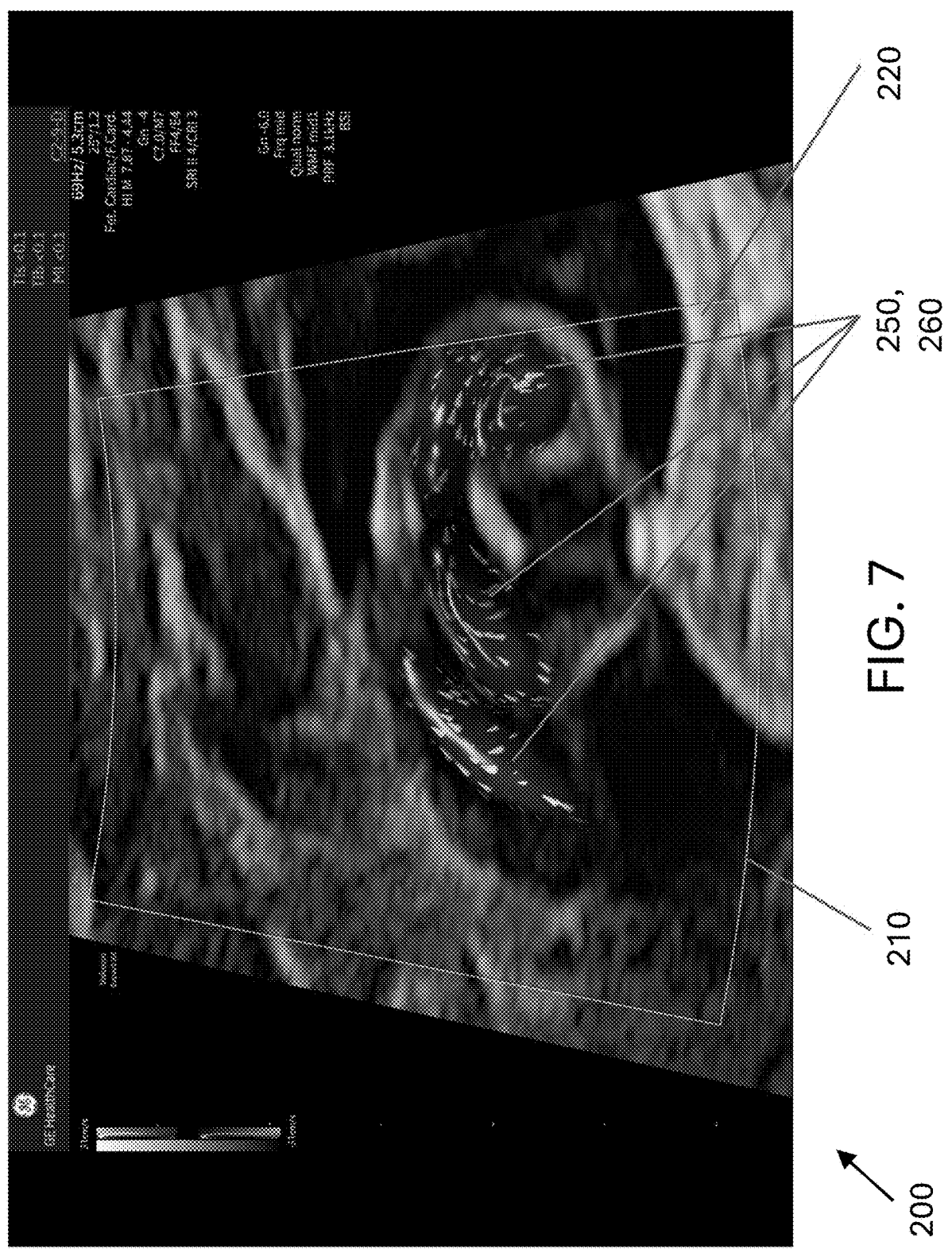
FIG. 7 depicts representations of the flow field of blood through the transparent blood vessels corresponding to FIG. 5, all of which is presented in context with the ultrasound image data of FIG. 2, according to embodiments.
Figure 11A:
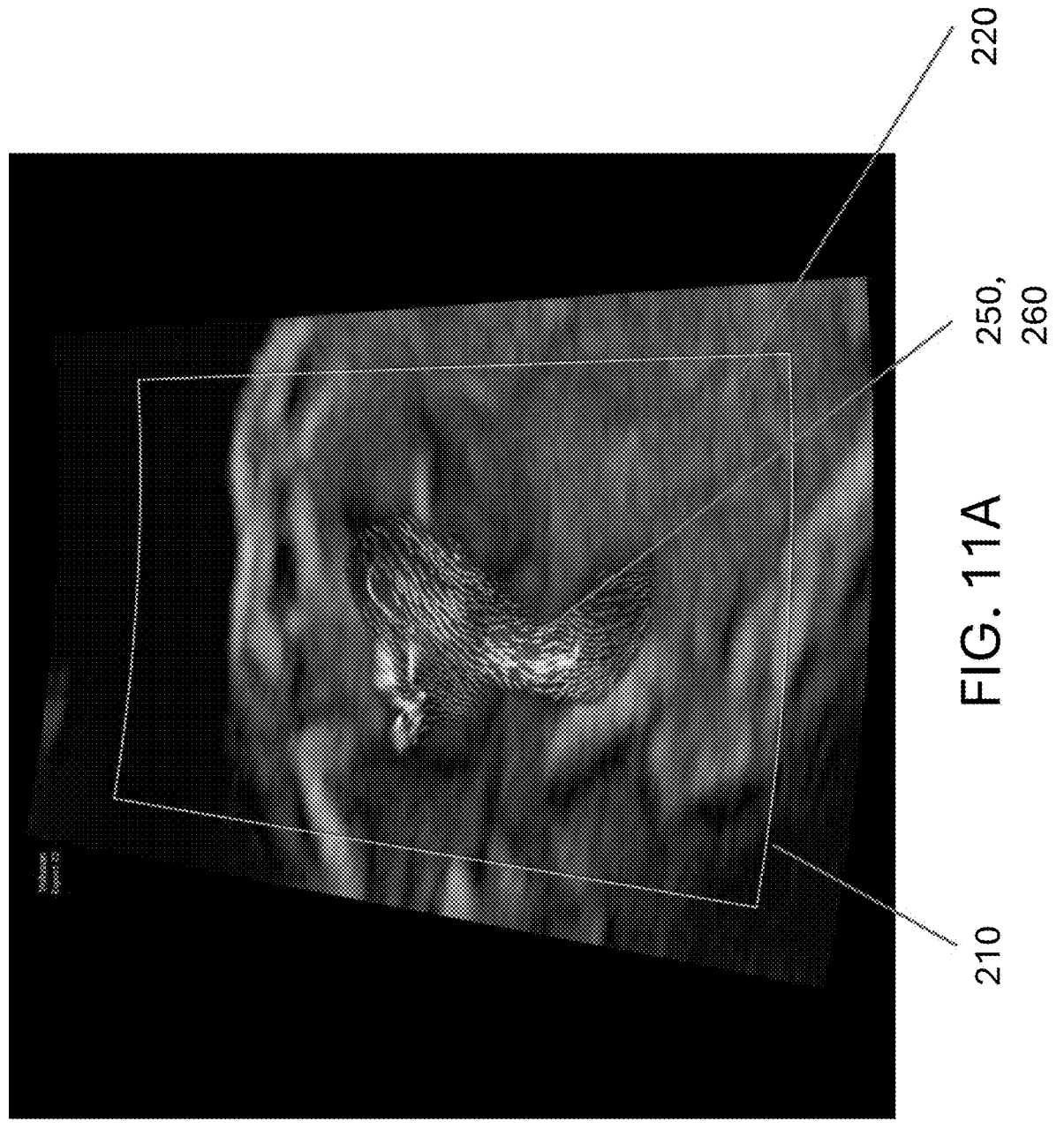
FIGS. 11A, 11B, and 11C depict examples of representations of a flow field of blood through transparent blood vessels, according to embodiments.
Figure 11B:
Figure 11C:
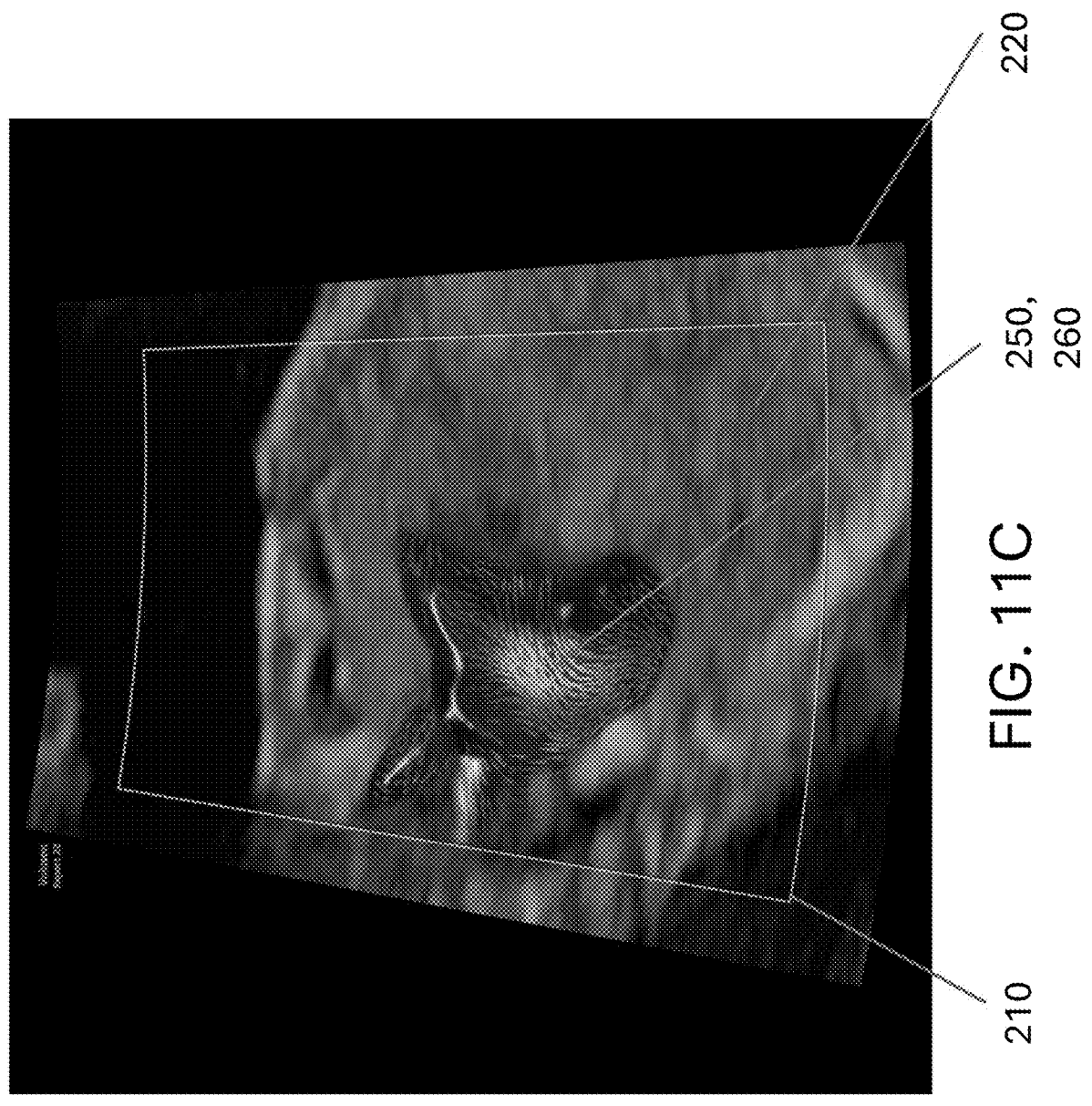

FIG. 7 combines the transparent blood vessels 250 of FIG. 5 with the representations 260 of the flow field of FIG. 6, for exemplary purposes. Certain principles of FIG. 7 are also described with respect to FIG. 8, which is an illustration in principle of a cross-section of a given blood vessel 250 shown in FIG. 7. For example, the representations 260 may be at any given height within or at an outer contour a blood vessel 250. Other potential embodiments relating to the representations 260 are described above in context of FIG. 8. FIGS. 11A, 11B, and 11C depict additional examples of transparent blood vessels 250 with representations 260.

Figure 9:
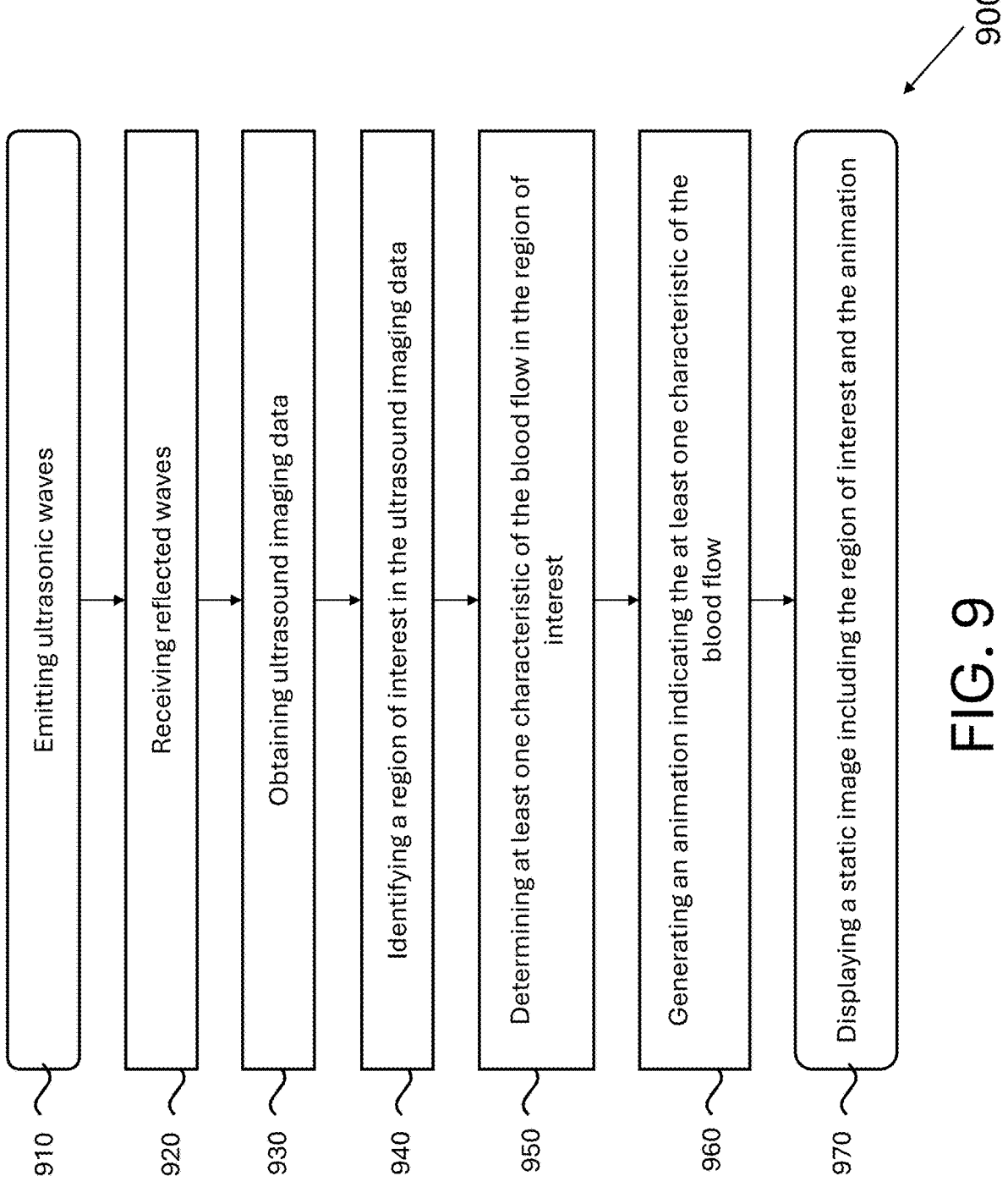
FIG. 9 is a flow chart illustrating exemplary steps that may be utilized for displaying an animation indicating at least one characteristic of a blood flow in an anatomical region of a patient.

FIG. 9 is a flowchart 900 illustrating exemplary steps that may be utilized for generating and displaying an animation in context of a static image to illustrate blood flow in an anatomical region. The flowchart 900 is described in context of ultrasound system 100 and the foregoing embodiments, but is not so limited. The steps may be performed in a different order or may overlap in time. Some steps may be omitted. Some of the steps may be performable by, for example, the signal processor 132 (e.g., any of steps 910, 920, 930, 940, 950, 960, or 970), including the blood speckle imaging processor 140 (e.g., any of steps 930, 940, or 950) and/or the visualization processor 150 (e.g., any of steps 960 or 970). Further, flowchart 900 is described with respect to blood flow, but may also be applicable to other types of fluid flows.

At step 910, ultrasonic waves are emitted (transmitted) from the ultrasound system 100. The waves are emitted from the transducer array 106 towards a patient's anatomical region that includes blood flow. At step 920, after the emitted waves are reflected by blood flow within the patient's anatomy, the reflected waves are received by the ultrasound system 100. The reflected waves are received by the transducer array 108. The reflected waves may be from the anatomical region and from the blood flow therein. The reflected waves may be received to obtain an imaging signal. The transducer array 106, 108 may include a piezoelectric layer that emits ultrasound waves and generates a signal based on reflected ultrasound waves. The transducer may further include a matching layer configured to have an acoustic impedance between a tissue of the anatomical region and a material of the transducer. The transducer may further include a damping block configured to absorb ultrasound energy. At step 930, ultrasound imaging data is obtained from the signals generated by the transducer array 108 when the reflected waves are received. The ultrasound imaging data that is obtained may be B-mode image data. The ultrasound imaging data (e.g., B-mode image data) may be a static image used in step 970. The ultrasound imaging data may include blood speckle imaging data. The blood speckle imaging data may correspond to a slot (e.g., frame) in which the static image is obtained. At step 940, an anatomical region in the ultrasound image data is identified. Such an anatomical region may be a patient's heart. Such an anatomical region may be identified by specifying a region of interest 210 in the ultrasound image data 200.

At step 950, at least one characteristic of the blood flow in the anatomical region is determined. Such characteristic(s) may be determined using blood speckle imaging data. Such characteristics may be specified in a flow field derived from blood speckle imaging data. Examples of characteristics include pathway (direction), speed, volume, and/or acceleration/deceleration. At step 960, an animation indicating the at least one characteristic of the blood flow in the anatomical region is generated. The animation may indicate the blood flow during a single time slot. At step 970, a static image including the anatomical region and the animation within the anatomical region is displayed on a display 134.

FIG. 10 is a flowchart 1000 illustrating exemplary steps that may be utilized for generating and displaying shaded and transparent patient anatomy in ultrasound image data, according to embodiments. The flowchart 1000 is described in context of ultrasound system 100 and the foregoing embodiments, but is not so limited. The steps may be performed in a different order or may overlap in time. Some steps may be omitted. Some of the steps may be performable by, for example, the signal processor 132 (e.g., any of steps 1010, 1020, 1030, 1040, 1050, or 1060), including the blood speckle imaging processor 140 (e.g., any of steps 1050, 1060) and/or the visualization processor 150 (e.g., any of steps 1010, 1020, 1030, 1040, 1050, or 1060). Further, flowchart 1000 is described with respect to blood vessels and blood flow, but may also be applicable to other types of anatomy and/or fluid flows.

At step 1010, ultrasound image data 200 is generated from reflected ultrasonic signals. Ultrasonic waves are emitted (transmitted) from the ultrasound system 100. The waves are emitted from the transducer array 106 towards a patient's anatomical region that includes blood vessels and flow. After the emitted waves are reflected by blood flow within the patient's anatomy, the reflected waves are received by the ultrasound system 100. The reflected waves are received by the transducer array 108. The reflected waves may be from the blood vessels and from the blood flow therein. The reflected waves may be received to obtain an imaging signal. The transducer array 106, 108 may include a piezoelectric layer that emits ultrasound waves and generates a signal based on reflected ultrasound waves. The transducer may further include a matching layer configured to have an acoustic impedance between a tissue of the anatomical region and a material of the transducer. The transducer may further include a damping block configured to absorb ultrasound energy. Ultrasound image data 200 is obtained from the signals generated by the transducer array 108 when the reflected waves are received. The ultrasound image data 200 that is obtained may include color Doppler image data and B-mode image data, for example. The ultrasound imaging data 200 (e.g., the B-mode image data) may include blood speckle imaging data. The blood speckle imaging data may correspond to a slot (e.g., frame) in which a static image is obtained. An anatomical region in the ultrasound image data 200 may be identified. Such an anatomical region may be a patient's heart including blood vessels. Such an anatomical region may be identified by specifying a region of interest 210 in the ultrasound image data 200.

At step 1020, a height map is determined according the reflected ultrasonic signals from different portions of a region of interest, such as blood vessels in the patient's heart. The height map may be determined from the ultrasound image data 200, such as color Doppler image data. Exemplary particulars for determining a height map are described above.

At step 1030, shaded image data is generated by shading the ultrasound image data 200 (e.g., color Doppler image data) according to the height map. The shaded image data may be generated according to the height map. Exemplary particulars of generating shaded image data are described above.

At step 1040, transparent blood vessels through which blood flow passes are generated. The transparent blood vessels may be generated with the shaded image data. Exemplary particulars of generating transparent blood vessels are described above. The transparent blood vessels may be displayed on display system 134. The transparent blood vessels may be displayed in context of other image data, such as B-mode image data.

At step 1050 a flow field of blood flow in the region of interest is determined. The flow field may be determined from BSI data. Exemplary particulars for determining a flow field are described above.

At step 1060, a representation of the flow field in the transparent blood vessels is displayed. The representations may be displayed within the transparent blood vessels. Exemplary particulars for displaying the representations are described above.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for enhancing sequential ultrasound images using deep learning.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

The invention claimed is:

1. An ultrasound system comprising:
a transmitter configured to emit ultrasonic energy towards a region of interest of a patient;
a receiver configured to receive ultrasonic signals reflected from the region of interest;
a processor configured to:
generate image data from the reflected ultrasonic signals;
determine a height map according the reflected ultrasonic signals from the region of interest; and
generate shaded image data by shading the image data according to the height map, such that regions of the image data that include blood flow are shaded to simulate a 3D effect, wherein the shaded effect includes transparent blood vessels through which the blood flow passes, wherein the transparent blood vessels are simulated by refracting virtual rays at locations of the height map; and
a display system configured to display the shaded image data.

2. The ultrasound system of claim 1, wherein the processor is further configured to:
determine a flow field of blood in the region of interest, wherein the flow field includes a plurality of vectors corresponding to a plurality of pathways of flows of the blood flow in the transparent blood vessels; and
display a representation of the flow field in the transparent blood vessels.

3. The ultrasound system of claim 2, wherein the representation of the flow field includes a plurality of arrows corresponding to the plurality of vectors.

4. The ultrasound system of claim 2, wherein the representation of the flow field includes an animation including a plurality of frames, wherein advancement of the frames indicates movement of the blood along the pathways of flows in the flow field.

5. The ultrasound system of claim 4, wherein the representation of the flow field includes virtual particles moving across the plurality of vectors.

6. The ultrasound system of claim 2, wherein the processor is further configured to display the flow field underneath an upper surface of the transparent blood vessels.

7. The ultrasound system of claim 2, wherein the representation of the flow field comprises different color information corresponding to different ones of the plurality of pathways along which the blood flows.

8. The ultrasound system of claim 1, wherein the processor is further configured to generate background ultrasound image data corresponding to tissue in the region of interest and displaying the shaded image data together with the ultrasound image data.

9. The ultrasound system of claim 1, wherein the processor is further configured to generate the transparent blood vessels according to the virtual rays and at least one of Snell's law and Beer's law.

10. The ultrasound system of claim 1, wherein the processor is further configured to generate the transparent blood vessels according to a Phong model.

11. A method of ultrasound imaging, the method comprising:
emitting, by a transmitter, ultrasonic energy towards a region of interest of a patient;
receiving, by a receiver, ultrasonic signals reflected from the region of interest;
generating, by a processor, image data from the reflected ultrasonic signals;
determining, by the processor, a height map according the reflected ultrasonic signals from the region of interest, and
generating, by the processor, shaded image data by shading the image data according to the height map, such that regions of the image data that include blood flow are shaded to simulate a 3D effect, wherein the shaded effect includes transparent blood vessels through which the blood flow passes, wherein the transparent blood vessels are simulated by refracting virtual rays at locations of the height map; and
displaying, by a display system, the shaded image data.

12. The method of claim 11, further comprising:
determining, by the processor, a flow field of blood in the region of interest, wherein the flow field includes a plurality of vectors corresponding to a plurality of pathways of flows of the blood flow in the transparent blood vessels; and
displaying, by the display system, a representation of the flow field in the transparent blood vessels.

13. The method of claim 12, wherein the representation of the flow field includes a plurality of arrows corresponding to the plurality of vectors.

14. The method of claim 12, wherein the representation of the flow field includes an animation including a plurality of frames, wherein advancement of the frames indicates movement of the blood along the pathways of flows in the flow field.

15. The method of claim 14, wherein the representation of the flow field includes virtual particles moving across the plurality of vectors.

16. The method of claim 12, further comprising displaying, by the display system, the flow field underneath an upper surface of the transparent blood vessels.

17. The method of claim 12, wherein the representation of the flow field comprises different color information corresponding to different ones of the plurality of pathways along which the blood flows.

18. The method of claim 12, further comprising generating, by the processor, the transparent blood vessels according to the virtual rays and at least one of Snell's law and Beer's law.

* * * * *